(12) United States Patent
Tanaka et al.

(10) Patent No.: US 11,431,084 B2
(45) Date of Patent: Aug. 30, 2022

(54) WIRELESS COMMUNICATION DEVICE, SENSOR DEVICE, AND WEARABLE DEVICE

(71) Applicants: OMRON Corporation, Kyoto (JP); OMRON HEALTHCARE Co., Ltd., Kyoto (JP)

(72) Inventors: Hirokazu Tanaka, Kyoto (JP); Hiroshi Miura, Kyoto (JP); Shohei Iwata, Kyoto (JP)

(73) Assignees: OMRON Corporation, Kyoto (JP); OMRON HEALTHCARE CO., LTD., Kyoto (JP)

( * ) Notice: Subject to any disclaimer, the term of this patent is extended or adjusted under 35 U.S.C. 154(b) by 7 days.

(21) Appl. No.: 16/940,519

(22) Filed: Jul. 28, 2020

(65) Prior Publication Data

US 2020/0358167 A1 Nov. 12, 2020

Related U.S. Application Data

(63) Continuation of application No. PCT/JP2019/004248, filed on Feb. 6, 2019.

(30) Foreign Application Priority Data

Feb. 14, 2018 (JP) .............................. JP2018-024405

(51) Int. Cl.
*H01Q 1/24* (2006.01)
*A61B 5/021* (2006.01)
(Continued)

(52) U.S. Cl.
CPC ............. *H01Q 1/243* (2013.01); *A61B 5/022* (2013.01); *A61B 5/02141* (2013.01); *H01Q 1/38* (2013.01); *H01Q 9/42* (2013.01)

(58) Field of Classification Search
CPC ................................. H01Q 1/32; H01Q 9/285
See application file for complete search history.

(56) References Cited

U.S. PATENT DOCUMENTS 9,912,044 B2  3/2018  Iijima et al.
2002/0163473 A1  11/2002  Koyama et al.
(Continued)

FOREIGN PATENT DOCUMENTS

CN  1843288 A  10/2006
CN  106362391 A  2/2017
(Continued)

OTHER PUBLICATIONS

Office Action dated May 7, 2021, in Chinese Patent Application No. 201980008016.8.
(Continued)

*Primary Examiner* — Graham P Smith
(74) *Attorney, Agent, or Firm* — Birch, Stewart, Kolasch & Birch, LLP

(57) ABSTRACT

A wireless communication device comprises: a substrate; an antenna circuit installed on the substrate; a communication circuit installed on the substrate electrically connected to the antenna circuit; and an energy supply unit installed on the substrate that supplies energy to the communication circuit, wherein the energy supply unit are installed on the substrate outside of a region defined around the antenna circuit; and the substrate is provided with a hole portion within the region, the hole portion passing through the substrate.

10 Claims, 10 Drawing Sheets

(51) Int. Cl.
  *A61B 5/022* (2006.01)
  *H01Q 1/38* (2006.01)
  *H01Q 9/42* (2006.01)

(56) References Cited

U.S. PATENT DOCUMENTS

| | | | |
|---|---|---|---|
| 2005/0078038 | A1 | 4/2005 | Takaki et al. |
| 2006/0164318 | A1* | 7/2006 | Lastinger ............... H01Q 1/521 343/841 |
| 2006/0255945 | A1* | 11/2006 | Egbert ............. G06K 19/07771 340/572.7 |
| 2007/0030154 | A1 | 2/2007 | Aiki et al. |
| 2009/0046020 | A1 | 2/2009 | Kato et al. |
| 2010/0048260 | A1* | 2/2010 | Bury .................. B60R 11/0241 455/575.1 |
| 2014/0206955 | A1* | 7/2014 | Stivoric ................ A61B 5/1118 600/301 |
| 2014/0285385 | A1 | 9/2014 | Aoki et al. |
| 2015/0109172 | A1 | 4/2015 | Iijima et al. |
| 2016/0049721 | A1 | 2/2016 | Aizawa et al. |
| 2017/0199497 | A1 | 7/2017 | Kuo et al. |
| 2018/0090826 | A1 | 3/2018 | Da Costa Bras Lima et al. |

FOREIGN PATENT DOCUMENTS

| | | |
|---|---|---|
| CN | 205923159 U | 2/2017 |
| CN | 106959600 A | 7/2017 |
| CN | 206363097 U | 7/2017 |
| EP | 2 989 965 A2 | 3/2016 |
| JP | H8-279710 A | 10/1996 |
| JP | H10-197662 A | 7/1998 |
| JP | 2003-35787 A | 2/2003 |
| JP | 2003-152582 A | 5/2003 |
| JP | 2004-28918 A | 1/2004 |
| JP | 2005-20074 A | 1/2005 |
| JP | 2005-94742 A | 4/2005 |
| JP | 2005-348136 A | 12/2005 |
| JP | 2006-288619 A | 10/2006 |
| JP | 2008-167899 A | 7/2008 |
| JP | 2012-154768 A | 8/2012 |
| JP | 2015-81825 A | 4/2015 |
| JP | 2016-40884 A | 3/2016 |
| JP | 3213636 U | 11/2017 |
| WO | WO 01/73889 A1 | 10/2001 |

OTHER PUBLICATIONS

International Search Report of the International Searching Authority for PCT/JP2019/004248 dated Mar. 5, 2019.
English translation of International Search Report of the International Searching Authority for PCT/JP2019/004248 dated Mar. 5, 2019.
International Preliminary Report on Patentability Chapter II for PCT/JP2019/004248 dated Jan. 16, 2020.
International Preliminary Report on Patentability and English translation of the Written Opinion of the International Searching Authority for International Application No. PCT/JP2019/004248, dated Aug. 20, 2020.
Chinese Office Action for Chinese Application No. 201980008016.8, dated Dec. 6, 2021, with an English translation.
Japanese Office Action for Japanese Application No. 2018-024405, dated Dec. 7, 2021, with an English translation.

* cited by examiner

_US 11,431,084 B2_

WIRELESS COMMUNICATION DEVICE, SENSOR DEVICE, AND WEARABLE DEVICE

CROSS-REFERENCE TO RELATED APPLICATIONS

This is a continuation of International Application PCT/JP2019/004248, with an international filing date of Feb. 6, 2019, and Application JP 2018-024405, with an international filing date of Feb. 14, 2018 filed by applicant, the disclosure of which is hereby incorporated by reference in its entirety

TECHNICAL FIELD

The present invention relates to an electronic device provided with an antenna.

BACKGROUND ART

In recent years, various wearable devices have entered the market. Wearable devices, also referred to as wearable computers, are portable computers that can be worn by a user.

Wearable devices can be used, for example, for user health management. Further, the wearable device may connect with another computer, such as a smart phone, to exchange information with the other computer. For example, some smart watches include sensors that measure the user's heart rate, blood pressure, and the like and can transmit this biological information to the smart phone.

There is a demand for wearable devices to be compact so that they can be comfortably worn by users, for example. For example, smart watches, a type of wearable device, are expected to have a similar compactness to that of normal wrist watches.

Wearable devices typically connect with other computers via wireless communication and therefore require an antenna. The antenna can be attached on the outside of the wearable device; however, this may result in the antenna being damaged when the wearable device is worn as well as requiring an electrically conductive structure between the antenna and a substrate and waterproofing of this structure. On the other hand, particularly when the case of a wearable device is compact and includes a metal material, there are many restrictions on the layout relating to disposing the antenna in the electronic device while maintaining the necessary emission efficiency, such as: antenna space saving, mitigation of electrical interference with another metal component, ensuring an emission port for electromagnetic waves, and the like; thus, disposing an antenna inside a wearable device, in particular one with a metal case, is difficult.

JP 2016-40884 A relates to technology for an antenna space saving arrangement. In this Patent Document, a metal bezel disposed in a case body of an electronic device and a metal ribbon included in an antenna are electromagnetically coupled, and an equivalent electrical length of the ribbon is set to be shorter than the ¼ wavelength.

Also, JP 2003-152582 A relates to technology for mitigating electrical interference between an antenna and another metal component. In this Patent Document, a wrist watch type information device is described in which an IC for wireless communication and a chip antenna are installed so as not to overlap in a plan view to reduce the possibility of electrical interference between the internal devices.

Furthermore, JP 2015-81825 A and JP 2003-35787 A relate to technology for ensuring an emission port for electromagnetic waves. JP 2015-81825 A describes a configuration in which an outer case is made of plastic and an antenna is arranged with a maximum radiation direction thereof intersecting a thickness direction of the outer case and arranged in a position not overlapping a metal bezel in the maximum radiation direction. This configuration prevents a satellite signal from a GPS satellite from being blocked by the bezel. JP 2003-35787 A describes a radio-controlled clock including: a non-metal main lid; and a back lid that includes a metal auxiliary lid, with a slit being formed by cutting a portion of the metal auxiliary lid to allow standard waves to pass through the slit.

SUMMARY OF INVENTION

An objective of the present disclosure is to install an antenna inside an electronic device while minimizing or preventing a reduction in emission efficiency.

According to a first aspect of the present disclosure, a wireless communication device comprises:
 a substrate;
 an antenna circuit installed on the substrate;
 a communication circuit installed on the substrate electrically connected to the antenna circuit; and
 an energy supply unit installed on the substrate that supplies energy to the communication circuit, wherein
 the communication circuit and the energy supply unit are installed on the substrate outside of a region defined around the antenna circuit; and
 the substrate is provided with a hole portion within the region, the hole portion passing through the substrate.

In the wireless communication device, the region is defined at or near a feed point of the antenna circuit on the substrate, and installation of the communication circuit and the energy supply unit is prohibited in the region. However, on the substrate, at least one of a plurality of hole portions for receiving a threaded member is formed in the region. In this way, according to the wireless communication device, a reduction in the emission efficiency due to a metal body being installed around the antenna circuit is suppressed, and limited space can be effectively used by preventing the region from being a completely dead space.

The wireless communication device according to the first aspect may further comprise:
 a support body; and
 a threaded member for fixing the substrate to the support body, the threaded member passing in the hole portion, wherein
 the threaded member includes a metal material. According to this wireless communication device, the hole portion in the region can be utilized to fix the substrate via screwing.

The wireless communication device according to the first aspect may further comprise:
 a case that houses at least the substrate, wherein
 the case includes a metal material; and
 the antenna circuit is installed in a manner such that parasitic capacitance occurs between the antenna circuit and the case. According to the wireless communication device (hereinafter referred to as the wireless communication device according to the second aspect of the present disclosure), the equivalent electrical length of the antenna circuit can be extended.

In the wireless communication device according to the second aspect, the antenna circuit may have an electrical length less than a ¼ wavelength of a target frequency. According to this wireless communication device, the volume occupied by the antenna circuit can be reduced, and the limited space inside the case can be effectively used.

According to a third aspect of the present disclosure, a sensor device comprises:

the wireless communication device according to the first aspect; and a sensor that measures a physical quantity and generates sensor data, wherein the communication circuit transmits the sensor data via the antenna circuit. According to the third aspect, the sensor device including the wireless communication device according to the first aspect can be provided.

According to a fourth aspect of the present disclosure, a sensor device comprises:

the wireless communication device according to the first aspect;

a sensor that measures a physical quantity and generates sensor data; and a display that displays the sensor data. According to the fourth aspect, the sensor device including the wireless communication device according to the first aspect can be provided.

In the sensor device according to the fourth aspect, the sensor may include a blood pressure monitor. According to the sensor device (hereinafter referred to as the sensor device according to the fifth aspect of the present disclosure), the user's blood pressure can be measured and displayed on the display.

The sensor device according to the fifth aspect may further comprise:

a case having a substantially cylindrical shape and including a first opening at a front surface and a second opening at a back surface, respectively;

a first cover member that blocks at least a portion of the first opening; and a second cover member that blocks at least a portion of the second opening, wherein the case includes a metal material;

the first cover member includes a light-transmitting material that allows light from the display to pass through;

the second cover member does not include any metal material in at least one region of the second cover member;

the case houses at least the substrate; and a first orthographic projection of the at least one region of the second cover member projected on a plane substantially parallel with the substrate contains a second orthographic projection of an installed region of the antenna circuit projected on the plane identical.

According to this sensor device (hereinafter referred to as the sensor device according to the sixth aspect of the present disclosure), the antenna circuit and the region of the second cover member not including a metal material overlap in a plan view. Thus, a reduction in the emission efficiency of the antenna circuit due to being disposed inside the case containing a metal material is minimized or prevented.

According to a seventh aspect of the present disclosure, a wearable device comprises:

the sensor device according to the sixth aspect; and a belt member connected to the case. The wearable device can measure the user's blood pressure, display the data on a display, and/or transmit the data via the wireless communication device according to the first aspect.

According to the present disclosure, an antenna can be installed inside an electronic device while minimizing or preventing a reduction in emission efficiency.

DESCRIPTION OF EMBODIMENTS

An embodiment according to an aspect of the present invention (hereinafter, also referred to as "the present embodiment") will be described below with reference to the drawings.

Note that elements that are the same as or similar to the elements described hereinafter are given the same or similar reference signs, and duplicate descriptions will be omitted.

1 APPLICATION EXAMPLE

Figure 1:
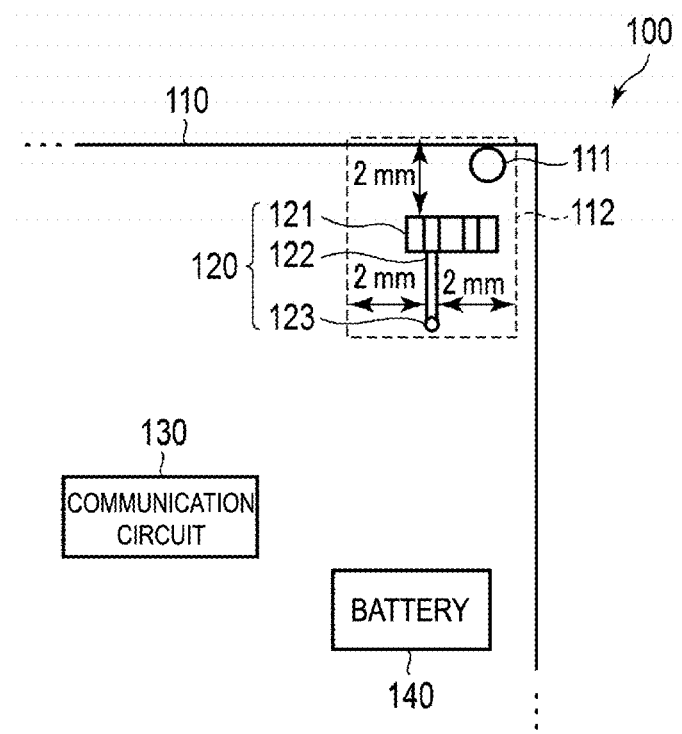
FIG. 1 is a diagram illustrating an application example of an electronic device according to an embodiment.

First, an application example of the present embodiment will be described with reference to FIG. 1. FIG. 1 schematically illustrates an application example of an electronic device according to the present embodiment. An electronic device 100 is, for example, a wearable device, such as a smartwatch, that displays, on a display not illustrated in FIG. 1, a user's blood pressure measured by a sensor unit not illustrated in FIG. 1 or transmits the user's blood pressure to another computer, such as a smart phone, connected with the electronic device 100. The electronic device 100 may be referred to as a wireless communication device when considering it is provided with an antenna circuit 120, which is a wireless communication interface (I/F), and a communication circuit 130 or may be referred to as a sensor device when considering it is provided with a sensor unit not illustrated FIG. 1.

As illustrated in FIG. 1, the electronic device 100 includes a substrate 110, the antenna circuit 120, the communication circuit 130, and a battery 140.

The substrate 110 is housed in a case of the electronic device 100 that is not illustrated in FIG. 1 and the antenna circuit 120 and the communication circuit 130 are provided on the substrate 110, and the battery 140 is installed.

The substrate 110 includes a plurality of hole portions passing through a front surface and a back surface of the substrate 110. One of these hole portions 111 is illustrated in FIG. 1. The substrate 110 may be fixed to a support body by being screwed together using the hole portion (111). Here, the support body may be the case of the electronic device 100 or may be another component such as, for example, a circuit case. Also, the threaded member for fixing the substrate 110 to the support body via the hole portion (111) may be metallic (in other words, a conductor) or include a metal material.

Metal bodies, such as the communication circuit 130 and the battery 140, affect the emission efficiency of the antenna circuit 120. A metal body at or near the location of an antinode of the antenna current induces a current in the opposite direction to the antenna current and reduces the apparent antenna current. This is thought to be one cause of reduction in the emission efficiency from the antenna circuit 120. The magnitude of the current induced by the metal body depends on the size of the metal body and the distance from the metal body to the antenna circuit 120. For this reason, the metal bodies are disposed outside of a prohibited region 112 of the substrate 110 defined around the antenna circuit 120.

Here, the prohibited region 112, for example, may be defined as an area roughly within a predetermined distance value from the antenna circuit 120, that is, an antenna element 121, a feed element 122, and a feed point 123. However, the area from both end portions of the antenna circuit 120 onward, specifically, the area from the end of the antenna element 121 onward (the open end of the antenna element 121 and a position of a node of the antenna current) and the area from the feed point 123 onward (a position of an antinode of the antenna current) may be excluded from the prohibited region 112. Furthermore, as described below, in the case in which the parasitic capacitance that occurs between the end of the antenna element 121 and the case of the electronic device 100 is used as a capacity hat connected to the antenna element 121, the area from the end of the antenna element 121 onward is included in the prohibited region 112. The predetermined value is, for example, 2 mm, but the predetermined value is not limited thereto. By providing the prohibited region 112 in this way, a reduction in emission efficiency, caused by a metal body being disposed near the antenna circuit 120, can be minimized or prevented.

Also, though the threaded member described above includes a metal material, it can be considered to be a floating conductor (also referred to as an insulated conductor) electrically isolated from the GND of the antenna circuit 120. Thus, the emission efficiency of the antenna circuit 120 is not greatly affected. Here, "floating conductor" can refer to a metal in a floating state or a metal that is electrically isolated from GND. Thus, by intentionally providing the hole portion 111 in the prohibited region 112, the prohibited region is prevented from being a completely dead space, and the limited space within the case of the electronic device 100 can be effectively utilized.

The antenna circuit 120 is designed to operate with microwaves, for example, electromagnetic waves at or near the 2.4 GHz band used by Bluetooth (trade name), Wi-Fi (trade name), and the like. Here, Bluetooth may include at least Bluetooth Low Energy (BLE), which is the version 4.0 specification. The ¼ wavelength of electromagnetic waves in the 2.4 GHz band is approximately 3 cm. However, as described below, by using the parasitic capacitance that occurs between the antenna element 121 and the case of the electronic device 100 as a capacity hat connected to the antenna element 121, the electrical length of the antenna circuit 120 can be pushed below the ¼ wavelength of the target frequency. Note that the target frequency of the antenna circuit 120 is not limited to the 2.4 GHz band.

The antenna circuit 120 is installed on the substrate 110 and includes the antenna element 121, the feed element 122, and the feed point 123. The antenna element 121 is fed from the feed point 123 via the feed element 122. The feed point 123 is the connection point between the feed element 122 and the substrate 110.

Because the antenna element 121 installed inside the small electronic device 100, it preferably has a compact size. Thus, for example, the antenna element 121 may be a chip antenna provided with a ¼ wavelength antenna, such as a monopole antenna, an inverted L antenna, an inverted F antenna, and the like. However, the antenna element 121 is not limited to being a ¼ wavelength antenna and, instead of being a chip antenna, may be a printed circuit board (PCB) antenna, a flexible printed circuit (FPC) antenna, a cast metal antenna, or the like. In an example in which the antenna element 121 is a chip antenna, the antenna element 121, for example, includes: a conductor material, which forms an inductor, and a dielectric material and a magnetic material disposed in a layered manner.

The feed element 122 is connected between the antenna element 121 and the feed point 123. The feed element 122, for example, may be a wire, a pipe, or the like including a conductor material such as copper or may be formed by applying, etching, or printing a conductive foil on the substrate 110.

The communication circuit 130 is installed on the substrate 110 and is electrically connected to the antenna circuit 120. The communication circuit 130 performs at least one of a signal transmission process and a signal reception process via the antenna circuit 120. The communication circuit 130 may include, for example, a modulator, a digital-to-analog converter, an upconverter, a filter, a power amplifier, and the like for realizing signal transmission. Also, the communication circuit 130 may include, for example, a low-noise amplifier, a filter, a downconverter, an analog-to-digital converter, a demodulator, and the like for realizing signal reception. Furthermore, the communication circuit 130 may also include a switch for switching between transmission and reception of antenna circuit 120.

The battery 140 is installed on the substrate 110 and supplies energy to various elements in the electronic device 100 including the communication circuit 130. The battery 140, for example, may be a rechargeable battery such as a lithium ion battery, but may be another type of rechargeable battery, or a primary battery. Also, instead of the battery 140, an energy supply unit, which has a broader meaning, may be used. This energy supply unit may correspond to the battery 140 and may supply power generated by energy harvesting such as vibration power generation, for example.

As described above, in the electronic device 100 according to the application example, the prohibited region 112 is defined at or near the feed point 123 of the antenna circuit 120 on the substrate 110, and installation of a metal body, such as the communication circuit 130 and the battery 140, is prohibited in the prohibited region 112. On the other hand, a floating conductor, such as a threaded member, for example, is permitted to be installed in the prohibited region 112. Thus, at least one of the plurality of hole portions (111) of the substrate 110 for receiving a threaded member is formed in the prohibited region 112. In this way, according to the electronic device 100, a reduction in the emission efficiency due to a metal body being installed near the antenna circuit 120 is suppressed, and the limited space within the case can be effectively used by preventing the prohibited region 112 from being a completely dead space. That is, according to the electronic device 100, performance necessary for wireless communication can be maintained and the minimum space required inside the case can be further reduced.

2 CONFIGURATION EXAMPLE

Figure 2:
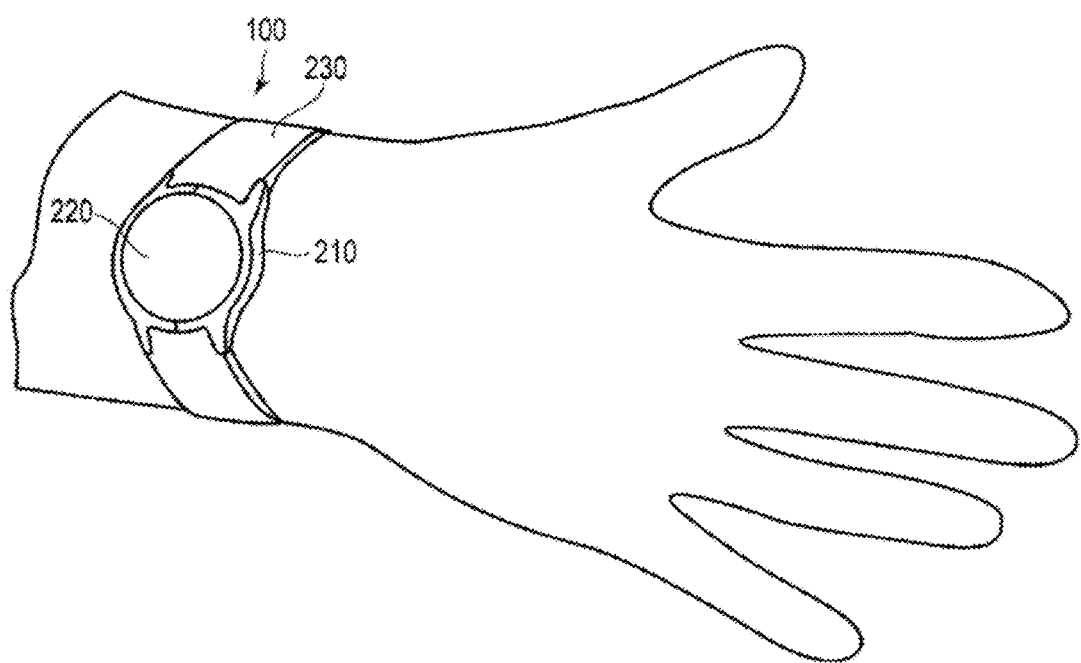
FIG. 2 is a perspective view illustrating an example of an electronic device according to an embodiment.

FIG. 2 illustrates an example of the appearance of the electronic device 100 according to an embodiment. Although the electronic device 100 is shaped similar to a wrist watch like a smart watch in FIG. 2, the shape of the electronic device 100 is not limited thereto. FIG. 2 illustrates a case 210 having a substantially cylindrical shape and including an opening on the front surface and the back surface, a glass lid 220 that blocks the opening (or a portion thereof) on the front surface of the case 210; and a belt member 230 connected to the case 210.

The case 210 is made of metal or may include a metal material (for example, a metal-plated non-metal material). This increases the durability of the case 210 and gives it a high-class design. Also, as described below with reference to FIG. 6, this also has the effect of artificially extending the electrical length of the antenna circuit 120.

The glass lid 220 includes glass or another light-transmitting material and allows light from a display not illustrated in FIG. 2 to pass through itself. That is, the user can view the display content of the display through the glass lid 220. Note that the glass lid 220 may simply be referred to as a cover member.

The belt member 230 is connected to the back surface of the case 210, the back lid that blocks the opening on the back surface (or a portion thereof), or another support body. The user can wear the electronic device 100 by wrapping the belt member 230 around the wrist such that the back surface of the case 210 faces inward. Note that, as described below, in the case in which the electronic device 100 includes a blood pressure monitor as one of its sensor units, the belt member 230 may be used as a cuff.

Figure 3:
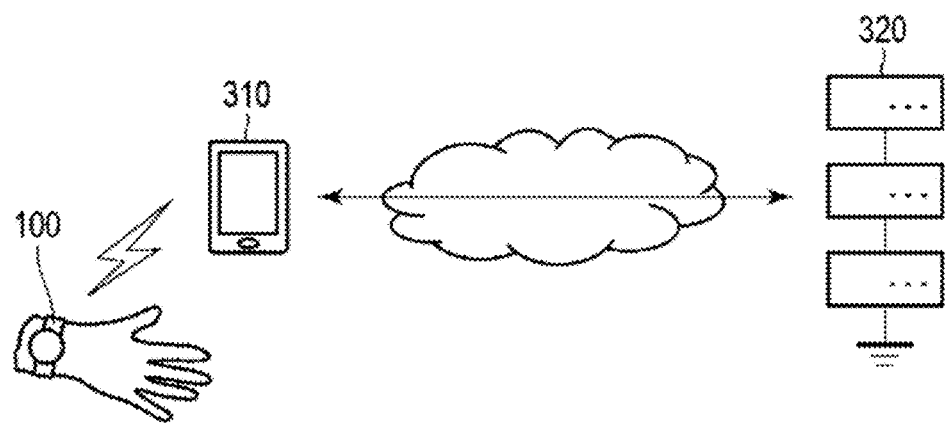
FIG. 3 is a diagram illustrating an example of a system including an electronic device according to an embodiment.

As illustrated in FIG. 3, the electronic device 100 is connected to a user device 310, which is another computer, such as a smart phone, tablet terminal, laptop, and the like. The electronic device 100 and the user device 310 may be connected using near-field wireless communication such as Bluetooth, for example. The electronic device 100 may, as necessary, transmit sensor data, such as blood pressure data, motion data (for example, acceleration data or angular velocity data), and step data calculated based on motion data, activity data, calories burned data, and the like, to the user device 310. Conversely, the electronic device 100 may receive various data, such as incoming notifications, mail notifications, and the like, from the user device 310 and display it on the display.

The user device 310 receives sensor data from the electronic device 100 using Bluetooth, WIFI, or the like. On the other hand, the user device 310 may transmit various data for display on the electronic device 100 to the electronic device 100. Also, the user device 310 may also be connected to a server 320 via a network, as illustrated in FIG. 3. However, the connection between the user device 310 and the server 320 is not required, and the electronic device 100 and the user device 310 may be connected together. The user device 310 transmits sensor data via a network to the server 320 using mobile communications, such as 3G, 4G, and the like; Wi-Fi; Wi-max; and the like.

In addition, the user device 310 may display the sensor data transmitted by electronic device 100 as a graph. The user device 310 may be installed with an application for managing sensor data.

The server 320 accumulates sensor data transmitted from the user device 310. The server 320, for example, may transmit the user's sensor data in response to access from an insurance company or a personal computer (PC) of a program operator as a provision for user's insurance subscription assessments, performance evaluation of health promoting programs, and the like.

Figure 4:
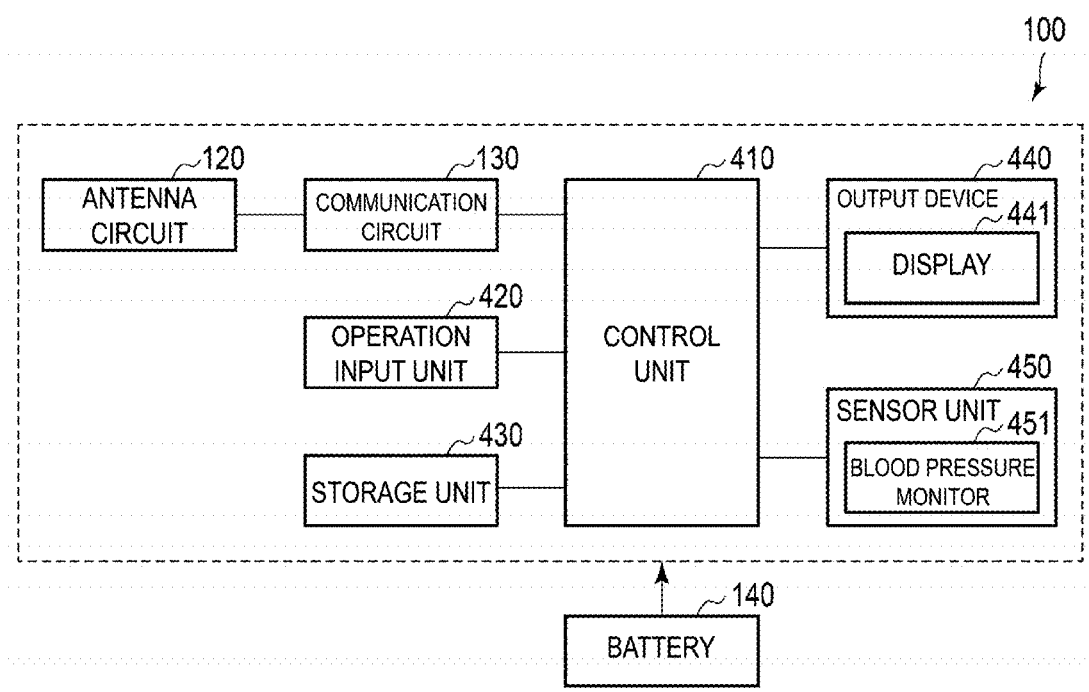
FIG. 4 is a block diagram illustrating an example of the hardware configuration of an electronic device according to an embodiment.

Next, an example of the hardware configuration of the electronic device 100 will be described with reference to FIG. 4. FIG. 4 schematically illustrates an example of the hardware configuration of the electronic device 100.

As illustrated in FIG. 4, the electronic device 100 according to the present embodiment may be a computer in which a control unit 410, the communication circuit 130, an operation input unit 420, a storage unit 430, an output device 440, and a sensor unit 450 are electrically connected. Furthermore, in the electronic device 100, the antenna circuit 120 is electrically connected to the communication circuit 130, and the battery 140 supplies energy to each element in FIG. 4.

The control unit 410 includes a central processing unit (CPU), a random access memory (RAM), a read only memory (ROM), and the like. The CPU deploys the program stored in the storage unit 430 in the RAM. The control unit 410 can execute various information processing by the CPU interpreting and executing the program.

For example, the control unit 410 receives the received data from the communication circuit 130 and conversely also sends the transmission data to the communication circuit 130. Also, the control unit 410 sends the output data to the output device 440 and instructs the sensor unit 450 to start/end the measurement. Furthermore, the control unit 410 receives the user's operation input from the operation input unit 420 and performs: an operation in response to this, such as a screen transition of a display 441 described below, transmission and reception of data to and from the user device 310, control of the start/end of the measurement by the sensor unit 450, and the like.

The operation input unit 420 is hardware configured to receive an operation input by a user. The operation input unit 420 may include, for example, a button, a crown, and the like provided on a side surface of the case 210 of the electronic device 100; or a touch-screen.

The storage unit 430 is a so-called auxiliary storage device, and can be, for example, a semiconductor memory such as a built-in flash memory. The storage unit 430 stores programs executed by the control unit 410, data used by the control unit 410 (for example, various sensor data), and the like.

The output device 440 may include the display 441 that displays video, still images, text, and the like and may include other devices such as speakers that output sound, musical pieces, and the like. The display 441, for example, is a liquid crystal display, an organic electroluminescence (EL) display, or the like. The display 441 may display sensor data, received data from the user device 310, and the like.

The sensor unit 450 measures a predetermined physical quantity, generates sensor data, and sends the data to the control unit 410. In addition to a blood pressure monitor 451 illustrated in FIG. 4, the sensor unit 450 may include a motion sensor (for example, an acceleration sensor, a gyro sensor, and the like); a camera (image sensor); a microphone; a pulse wave sensor; an environment sensor (for example, a temperature sensor, a humidity sensor, an atmospheric pressure sensor, and the like); and the like. Sensor data is not limited to raw sensing data and may also include data generated by correcting or processing.

The blood pressure monitor 451 can include a blood pressure monitor capable of continuously measuring the user's blood pressure every beat (hereinafter, referred to as a continuous blood pressure monitor). The continuous blood pressure monitor may continuously measure the user's blood pressure from the pulse transmit time (PTT), or the continuous measurement may be achieved by a tonometry method or another technique.

The blood pressure monitor 451 may also include, instead of or in addition to the continuous blood pressure monitor, a blood pressure monitor not capable of continuous measurement (hereinafter, referred to as a non-continuous blood pressure monitor). The non-continuous blood pressure monitor can be, for example, an oscillometric blood pressure monitor. An oscillometric blood pressure monitor detects the pressure pulse wave during the step of depressurizing the cuff after pressurization and determines the user's blood pressure based on this. In the case in which the blood pressure monitor 451 includes an oscillometric blood pressure monitor, the belt member 230 of the electronic device 100 may be used as a cuff, as previously described.

A non-continuous blood pressure monitor (in particular, an oscillometric blood pressure monitor) tends to have high measurement accuracy compared to a continuous blood pressure monitor. Thus, the blood pressure monitor, for example, may activate the non-continuous blood pressure monitor instead of the continuous blood pressure monitor when, as a trigger, a condition is satisfied (for example, the user's blood pressure data measured by the continuous blood pressure monitor displays a predetermined state) and measure the blood pressure data with higher accuracy.

Note that, with regard to a specific hardware configuration of the electronic device 100, components can be omitted, replaced, and added as appropriate according to the embodiment. For example, the control unit 410 may include a plurality of processors, and the electronic device 100 may be composed of a plurality of information processing devices, and the like.

Figure 5:
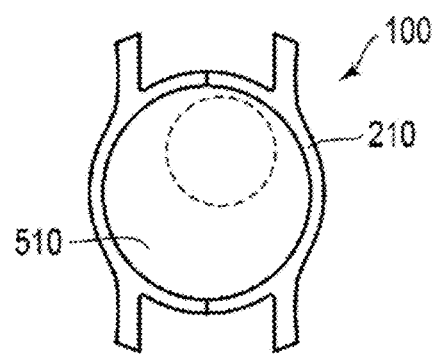
FIG. 5 is a bottom view illustrating an example of an electronic device according to an embodiment.

FIG. 5 illustrates an example of the back surface of the electronic device 100. As illustrated in FIG. 5, in electronic device 100, the opening (or at least a portion thereof) on the back surface side of the case 210 is blocked by a back lid 510. Note that the case 210 and the back lid 510 need not necessarily be separate components and may be formed integrally.

The back lid 510 may be made of metal but from the perspective of minimizing or preventing a reduction in emission efficiency, preferably does not include any metal material or does not include any metal material in at least one region thereof. The at least one region is, for example, defined as the region overlapping the installed region of the antenna circuit 120 as seen in a plan view. Specifically, an orthographic projection of the region of the back lid 510 not including a metal material projected on a plane substantially parallel with the substrate 110 contains an orthographic projection of the installed region of the antenna circuit 120 projected on the same plane. That is, the back lid 510 (or at least one region thereof) can be used as an emission port for electromagnetic waves transmitted and received by the antenna circuit 120. The back lid 510 may be connected to the case 210 by being screwed together, for example. The back lid 510 may also simply be referred to as a cover member.

Figure 6:
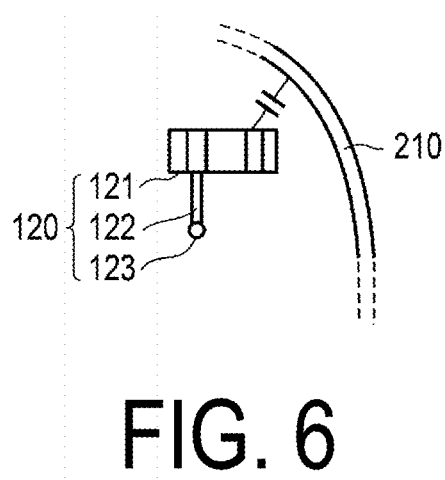
FIG. 6 is an explanatory diagram illustrating the relationship between an antenna circuit and a case in an electronic device according to an embodiment.

Furthermore, as described above, the case 210 has an effect of artificially extending the electrical length of the antenna circuit 120. In the region of the substrate 110 corresponding to the dashed line region of FIG. 5, as illustrated in FIG. 6, the end of the antenna element 121 is disposed in the proximity of a portion of the case 210, and parasitic capacitance occurs between the two. This parasitic capacitance may be considered a capacity hat and may equivalently extend the electrical length of antenna circuit 120 while minimizing or preventing a reduction in the emission efficiency of antenna circuit 120. The distance between the two are set to, for example, 2 mm or less, but is not limited thereto.

Figure 7:
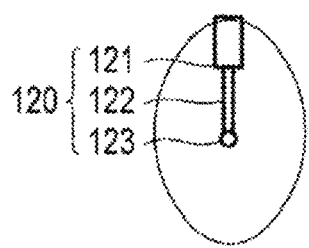
FIG. 7 is a diagram illustrating an example of the distribution of an antenna current in the case in which the antenna circuit operates alone.
Figure 8:
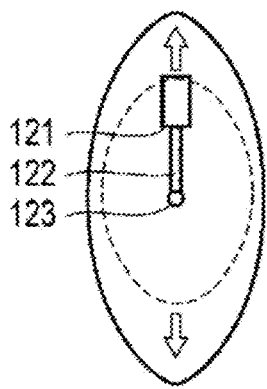
FIG. 8 is a diagram illustrating an example of the distribution of an antenna current in the case in which the antenna circuit is connected to a capacity hat.

When the antenna circuit 120 operates alone, as illustrated in FIG. 7, the antenna current is distributed such that the vicinity of the end (open end) of the antenna element 121 is a node and the vicinity of the feed point 123 is an antinode. On the other hand, when the capacity hat is connected to the antenna element 121, the position of the node of the antenna current extends further out from that illustrated in the example of FIG. 7. This is illustrated in FIG. 8. This is equivalent to extending the electrical length of the antenna circuit 120. Thus, even in the case in which the electrical length of the antenna circuit 120 is set shorter than the ¼ wavelength of the target frequency, the resonant frequency when the antenna circuit 120 operates can be brought close to the target frequency.

Figure 9:
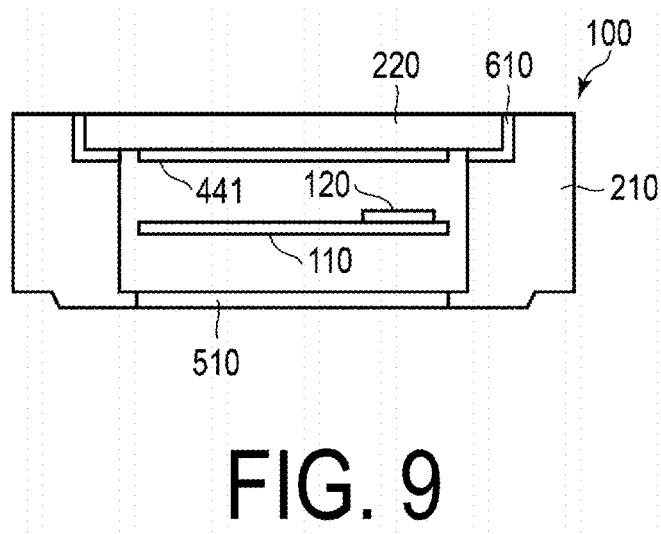
FIG. 9 is a cross-sectional view illustrating an example of an electronic device according to an embodiment.

FIG. 9 illustrates an example of the cross-sectional structure of the electronic device 100. FIG. 9 illustrates an example of a cross-section of the electronic device 100 sectioned through the antenna circuit 120 in a plan view substantially perpendicular to the surface of the electronic device 100. The case 210 include a projection portion that is provided on an inner wall surface connecting to the openings and that projects toward the opening inner side. The glass lid 220 is supported by the projection portion of the case 210 with a gap formed therebetween.

An insulating member 610 fills the gap between the projection portion of the case 210 and the glass lid 220. The insulating member 610 seals the gap and increases waterproofing and dustproofing and forms an electrical slit, through which electromagnetic waves can pass, between the internal space and the external space of the case 210. The electrical slit can be used as an emission port for electromagnetic waves transmitted and received by the antenna circuit 120. Note that a gap may be formed between the insulating member 610 and the display 441 as illustrated in FIG. 9, or the insulating member 610 may be in contact with the display 441.

The length of the emission port is preferably equal to or greater than the ¼ wavelength of the target frequency. In the case in which the glass lid has a disk shape with a diameter of approximately 3 cm, an emission port the size of the outer circumference, i.e., approximately 10 cm, can be secured. This is a length greater than 3 cm, which is the length of the emission port required by electromagnetic waves in the 2.4 GHz band. The electrical slit is formed utilizing the gap between components of the electronic device 100 and does not require the case 210 or other components to be processed, for example, cut or the like. Thus, there is little limitation on the flexibility of the design of the electronic device 100.

Actions and Effects

As described above, in the electronic device according to an embodiment, the antenna circuit, the communication circuit, and the battery are installed on the substrate. However, the communication circuit and the battery are prohibited from being installed within the prohibited region of the substrate defined around the antenna circuit. On the other hand, in the electronic device, the substrate includes a hole portion in the prohibited region for fixing via screwing that passing through the front surface and the back surface. In this way, according to the electronic device, a reduction in the emission efficiency due to a metal body being installed near the antenna circuit is suppressed, and the limited space within the case can be effectively used by preventing the prohibited region from being a completely dead space. That is, according to the electronic device, performance necessary for wireless communication can be maintained and the minimum space required inside the case can be further reduced.

3 MODIFIED EXAMPLE

While embodiments of the present invention have been described in detail above, the foregoing description is merely illustrative of the present invention in all respects. Of course, various modifications and variations can be made without departing from the scope of the present invention. For example, the following changes are possible. Note that, in the following, the same reference numerals are used for components similar to those of the above-described embodiment, and descriptions thereof will be omitted as appropriate. The following modified examples can be combined as appropriate.
4.1

Figure 10:
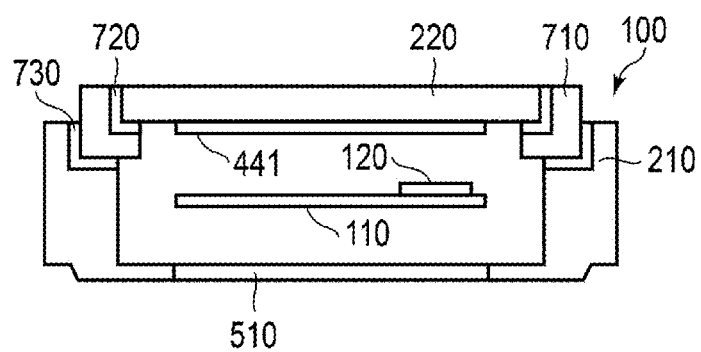
FIG. 10 is a cross-sectional view of a modified example of the example illustrated in FIG. 9.

Although FIG. 9 illustrates a cross-sectional structure of the electronic device 100, a modified example thereof is illustrated in FIG. 10. FIG. 10 illustrates another example of a cross-section of the electronic device 100 sectioned through the antenna circuit 120 in a plan view substantially perpendicular to the surface of the electronic device 100. Similar to the example illustrated in FIG. 9, the case 210 includes a projection portion that is provided on the inner wall surface connecting to the opening and that projects toward the opening inner side. However, rather than the projection portion supporting the glass lid 220, the projection portion supports an annular frame 710 with a gap formed therebetween.

The annular frame 710 is a substantially cylindrical frame body including an opening on the front surface and the back surface. The annular frame 710 includes a projection portion that is provided on the inner wall connecting to the opening and that projects toward the opening inner side. The glass lid 220 is supported by the projection portion with a gap formed therebetween. The annular frame 710 serves as a cushioning when an external force is applied to the case 210 and is transmitted to the glass lid 220 or as decoration. Also, the annular frame 710 has an effect of increasing the number of electrical slits as described below. The annular frame 710 may also be referred to as a support member as it supports (indirectly) the glass lid 220.

An insulating member 720 fills the gap between the projection portion of the annular frame 710 and the glass lid 220. Also, an insulating member 730 fills the gap between the projection portion of the case 210 and the annular frame 710. The insulating member 720 and the insulating member 730 seal the gap and increase waterproofing and dustproofing and form electrical slits, through which electromagnetic waves can pass, between the internal space and the external space of the case 210. These electrical slits can be used as emission ports for electromagnetic waves transmitted and received by the antenna circuit 120. Note that a gap may be formed between the insulating member 720 and the insulating member 730 and the display 441 as illustrated in FIG. 10, or the insulating member 720 and the insulating member 730 may be in contact with the display 441.

The length of the emission port is preferably greater than or equal to the ¼ wavelength of the target frequency. In the case in which the glass lid has a disk shape with a diameter of approximately 3 cm, two emission ports the size of the outer circumference, i.e., approximately 10 cm, can be secured. This is a greater length than 3 cm, which is the length of the emission port required by electromagnetic waves in the 2.4 GHz band. The electrical slits are formed utilizing the gap between components of the electronic device 100 and does not require the case 210 or other components to be processed, for example, cut or the like. Thus, there is little limitation on the flexibility of the design of the electronic device 100.

Note that in the case in which one of the emission ports is unnecessary, the insulating member 720 or the insulating member 730 may be omitted. Also, the opening is not limited to the electrical slit formed between components described with reference FIGS. 9 and 10. In the case in which the electronic device 100 includes an opening for a different purpose such as non-contact power feeding, for example, the opening can be used as an emission port for electromagnetic waves transmitted and received by the antenna circuit 120. Furthermore, even in a case in which the size of the emission port is less than the ¼ wavelength of the target frequency, the reduction in the emission efficiency can be minimized or prevented by installing the antenna circuit 120 at or near the emission port.

However, the embodiments described above are merely illustrative of the invention in all respects. Of course, various modifications and variations can be made without departing from the scope of the present invention. In other words, specific configurations in accordance with an embodiment may be adopted as appropriate at the time of carrying out the present disclosure. Note that although data appearing in the present embodiment will be described using natural language, the data is more specifically designated by pseudo-language, commands, parameters, machine language, and the like that are recognizable by a computer.

A part or the entirety of the embodiment can be described, as described in the following supplementary notes in addition to the scope of the claims, but the present invention is not limited thereto.

A wireless communication device (100) comprising:
a substrate (110);
an antenna circuit (120) installed on the substrate;
a communication circuit (130) installed on the substrate electrically connected to the antenna circuit; and
an energy supply unit (140) installed on the substrate that supplies energy to the communication circuit, wherein
the communication circuit and the energy supply unit are installed on the substrate outside of a region (112) defined around the antenna circuit; and
the substrate is provided with a hole portion (111) within the region, the hole portion passing through the substrate.

REFERENCE SIGNS LIST

100 . . . Electronic device
110 . . . Substrate
111 . . . Hole portion
112 . . . Prohibited region
120 . . . Antenna circuit
121 . . . Antenna element
122 . . . Feed element 123 . . . Feed point
130 . . . Communication circuit
140 . . . Battery
210 . . . Case
220 . . . Glass lid
230 . . . Belt member
310 . . . User device
320 . . . Server
410 . . . Control unit
420 . . . Operation input unit
430 . . . Storage unit
440 . . . Output device
441 . . . Display
450 . . . Sensor unit
451 . . . Blood pressure monitor
510 . . . Back lid
610, 720, 730 . . . Insulating member
710 . . . Annular frame

The invention claimed is:

1. A wireless communication device comprising:
a substrate;
an antenna circuit installed on the substrate;
a communication circuit installed on the substrate, the communication circuit being electrically connected to the antenna circuit; and
an energy supply unit installed on the substrate, the energy supply unit supplying energy to the communication circuit, wherein
the communication circuit and the energy supply unit are installed on the substrate outside of a region defined around the antenna circuit, the region is on the substrate and is larger than an installed region of the antenna circuit, and the antenna circuit, the communication circuit, and the energy supply unit include a metal material; and
the substrate is provided with a hole portion within the region, the hole portion passing through the substrate.

2. The wireless communication device according to claim 1, further comprising:
a support body; and
a threaded member for fixing the substrate to the support body, the threaded member being inserted in the hole portion, wherein
the threaded member includes a metal material.

3. The wireless communication device according to claim 1, further comprising:
a case that houses at least the substrate, wherein
the case includes a metal material; and
the antenna circuit is installed in a manner such that parasitic capacitance occurs between the antenna circuit and the case.

4. The wireless communication device according to claim 3, wherein
the antenna circuit have an electrical length less than a ¼ wavelength of a target frequency.

5. A sensor device comprising:
the wireless communication device according to claim 1; and
a sensor that measures a physical quantity and generates sensor data, wherein
the communication circuit transmits the sensor data via the antenna circuit.

6. A sensor device comprising:
the wireless communication device according to claim 1;
a sensor that measures a physical quantity and generates sensor data; and
a display that displays the sensor data.

7. The sensor device according to claim 6, wherein
the sensor includes a blood pressure monitor.

8. A sensor device comprising:
a wireless communication device;
a sensor that measures a physical quantity and generates sensor data; and
a display that displays the sensor data, wherein
the sensor includes a blood pressure monitor,
the wireless communication device comprises:
a substrate;
an antenna circuit installed on the substrate;
a communication circuit installed on the substrate, the communication circuit being electrically connected to the antenna circuit; and
an energy supply unit installed on the substrate, the energy supply unit supplying energy to the communication circuit, wherein
the communication circuit and the energy supply unit are installed on the substrate outside of a region defined around the antenna circuit, the region being larger than an installed region of the antenna circuit; and
the substrate is provided with a hole portion within the region, the hole portion passing through the substrate, and
the sensor device further comprises:
a case having a substantially cylindrical shape and including a first opening at a front surface and a second opening at a back surface, respectively;
a first cover member that blocks at least a portion of the first opening; and
a second cover member that blocks at least a portion of the second opening, wherein
the case includes a metal material;
the first cover member includes a light-transmitting material that allows light from the display to pass through;
the second cover member does not include any metal material in at least one region of the second cover member;
the case houses at least the substrate; and
a first orthographic projection of the at least one region of the second cover member projected on a plane substantially parallel with the substrate contains a second orthographic projection of an installed region of the antenna circuit projected on the plane identical.

9. A wearable device comprising:
the sensor device according to claim 8; and
a belt member connected to the case.

10. A sensor device comprising:
a wireless communication device;
a sensor that measures a physical quantity and generates sensor data; and
a display that displays the sensor data,
wherein the sensor includes a blood pressure monitor,
wherein the wireless communication device comprises:
a substrate;
an antenna circuit installed on the substrate;
a communication circuit installed on the substrate, the communication circuit being electrically connected to the antenna circuit; and
an energy supply unit installed on the substrate, the energy supply unit supplying energy to the communication circuit, wherein the communication circuit and the energy supply unit are installed on the substrate outside of a region defined around the antenna circuit, the substrate is provided with a hole portion within the region, the hole portion passing through the substrate, and wherein the sensor device further comprises:
a case having a substantially cylindrical shape and including a first opening at a front surface and a second opening at a back surface, respectively;
a first cover member that blocks at least a portion of the first opening; and
a second cover member that blocks at least a portion of the second opening, wherein the case includes a metal material,
the first cover member includes a light-transmitting material that allows light from the display to pass through,
the second cover member does not include any metal material in at least one region of the second cover member,
the case houses at least the substrate, and
a first orthographic projection of the at least one region of the second cover member projected on a plane substantially parallel with the substrate contains a second orthographic projection of an installed region of the antenna circuit projected on the plane identical.

* * * * *